United States Patent [19]

Speranza et al.

[11] Patent Number: 4,885,390

[45] Date of Patent: Dec. 5, 1989

[54] ALKOXYLATED ETHYLENE GLYCOL DIAMINE BOTTOMS PRODUCTS FOR RIGID URETHANE FOAMS

[75] Inventors: George P. Speranza; Michael E. Brennan, both of Austin; Jiang-Jen Lin, Round Rock, all of Tex.

[73] Assignee: ARCO Chemical Technology, Inc., Wilmington, Del.

[21] Appl. No.: 117,559

[22] Filed: Oct. 30, 1987

[51] Int. Cl.[4] ............................................. C07C 89/02
[52] U.S. Cl. ..................................... 564/475; 564/476
[58] Field of Search ........................ 564/475, 476, 471

[56] References Cited

U.S. PATENT DOCUMENTS

| | | | |
|---|---|---|---|
| 2,792,372 | 5/1957 | Dickson | 564/475 |
| 2,884,459 | 4/1959 | Kirkpatrick et al. | 564/475 |
| 3,297,597 | 1/1967 | Edwards | 260/2.5 |
| 4,115,304 | 9/1978 | Chadwick | 564/475 |
| 4,465,858 | 8/1984 | Cuscurida | 564/477 |
| 4,479,010 | 10/1984 | Cuscurida | 564/477 |
| 4,485,196 | 11/1984 | Speranza | 521/172 |

Primary Examiner—Werren H. Lone
Attorney, Agent, or Firm—David L. Mossman; Steve Rosenblatt

[57] ABSTRACT

Novel amino polyols made by alkoxylating ethylene glycol diamine bottoms products, such as triethylene glycol diamine bottoms products, and tetraethylene glycol diamine bottoms products are described. For example, these bottoms products, alone or together, maybe propoxylated in a non-catalytic reaction to give amino polyols that are useful in producing rigid polyurethane foams. The resultant foams have better K-factors and a higher percentage of closed cells than comparable foams made with conventional amino polyols.

12 Claims, No Drawings

ALKOXYLATED ETHYLENE GLYCOL DIAMINE BOTTOMS PRODUCTS FOR RIGID URETHANE FOAMS

FIELD OF THE INVENTION

The invention relates to alkoxylated bottoms products, and more particularly relates to alkoxylated ethylene glycol diamine bottoms products, which are found to be useful components in rigid polyurethane foams.

BACKGROUND OF THE INVENTION

It is known to prepare triethylene glycol diamine and tetraethylene glycol diamine. These compounds are known under the tradenames JEFFAMINE ®EDR-148 and JEFFAMINE ®EDR-192, respectively, made by Texaco Chemical Co. These materials are useful as intermediates in the preparation of hydrophilic nylon resins, and as epoxy curing agents. However, in the production of triethylene glycol diamine and tetraethylene glycol diamine, there are also produced significant volumes of bottoms products which are not useful for the same purposes as the primary products. It would therefor be beneficial if a use for these otherwise undesirable bottoms products could be discovered.

The general concept of alkoxylating amines is known. For example, see U.S. Pat. Nos. 4,465,858 and 4,479,010, incorporated by reference herein, which describe procedures for alkoxylating polyoxyalkyleneamines.

Conventional amino polyols which are known to be useful in the preparation of rigid polyurethane foams include THANOL ®R-350-X, an aromatic amino polyol having a hydroxyl number of 530 produced by Texaco Chemical Co., described in U.S. Pat. No. 3,297,597 incorporated by reference herein; QUADROL ® offered by BASF, which has the structure:

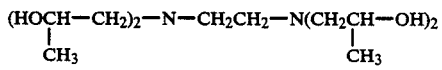

and VORANOL ®800 offered by Dow Chemical Co., which has the structure:

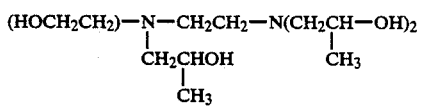

SUMMARY OF THE INVENTION

Accordingly, it is an object of the present invention to provide a productive use for the bottoms products from the production of triethylene glycol diamine and tetraethylene glycol diamine.

It is another object of the present invention to provide novel amino polyols from the otherwise unsuitable bottoms products described above.

It is yet another object of the invention to provide novel amino polyols from the aforementioned bottoms products that will produce rigid polyurethane foams having better insulation values (K-factors) and a higher percentage of closed cell structures than foams made from other, known amino polyols, wherein the other properties of the rigid foams are comparable to those made with conventional polyols.

In carrying out these and other objects of the invention, there is provided, in one form, amino polyols prepared by the process of reacting an alkylene oxide with ethylene glycol diamine bottoms products. The alkylene oxide may be ethylene oxide, propylene oxide, butylene oxide and mixtures thereof, while the ethylene glycol diamine bottoms products may be triethylene glycol bottoms products, tetraethylene glycol bottoms products, and mixtures thereof.

DETAILED DESCRIPTION OF THE INVENTION

The inventors have surprisingly discovered that the bottoms products from the synthesis of triethylene glycol diamine, the bottoms products from the manufacture of tetraethylene glycol diamine and, in particular, mixtures thereof may be alkoxylated to give amino polyols that are useful in preparing rigid polyurethane foams. Not only do the resultant rigid urethane foams have comparable properties to foams made from known amino polyol crosslinkers, but the rigid foams made from these new polyols have better insulation values or K-factors and a greater percentage of closed cells than the foams made from the conventional amino polyols. Of particular interest are the amino polyols obtained when the residues obtained from the two processes are mixed first and then alkoxylated, for exceptional foams are obtained when the resultant amino polyols are used in rigid urethane foams.

As noted, the reactants useful in making the amino polyols of the present invention are bottoms products from the production of ethylene glycol diamines, including bottoms products from the production of triethylene glycol diamine, tetraethylene glycol diamine and mixtures thereof. These will be described in more detail later. The other reactant should be an alkylene oxide, such as ethylene oxide, propylene oxide, butylene oxide and mixtures thereof. It is anticipated that alkylene oxides having up to 8 carbon atoms may find utility in these unique amino polyols. The resultant products, the novel amino polyols of the present invention, boil at a higher temperature than the diamines and thus are easy to separate by stripping.

The reaction may be conducted in either a batch or continuous mode. The alkoxylations should be conducted at a temperature in the range of about 80° to 150° C. and at a pressure in the range from about atmospheric to about 30 to 40 atmospheres. Preferred reaction conditions are: a temperature of about 90° to about 120° C., and a pressure from about 1 to 5 atmospheres. No catalyst is required for the reaction. The mole ratio of alkylene oxide to bottoms product may range from about 3:1 to about 6:1, with a preferred range being from about 4:1 to about 6:1, or even from about 4:1 to about 5:1, based on active amine content, in other words, the number of active hydrogens bonded to nitrogen.

Bottoms products from any process will vary somewhat, and are thus difficult to define with precision. Bottoms products from the preparation of triethylene glycol diamine by the reduction with ammonia of triethylene glycol will vary depending on the temperature and pressure which they are subjected to. Some of the bottoms products, which could be taken overhead, include structures such as the following:

NH$_2$CH$_2$CH$_2$OCH$_2$CH$_2$—OCH$_2$CH$_2$—NH—CH$_2$CH$_2$OCH$_2$CH$_2$—CH$_2$CH$_2$OH;

and so forth.

The invention will be further illustrated by the following examples which are not intended to limit the invention. The products used in Example 1 had the following analysis:
Total acetylatables: 6.72 meq/g
Total amine: 4.37 meq/g
Secondary and tertiary amines: 1.83 meq/g

EXAMPLE 1

Propoxylation of Triethylene Glycol Diamine Residues

To a one liter stirred autoclave was added 300 g of the bottoms product noted above. The contents were flushed twice with nitrogen, and 40 ml of propylene oxide were added. The materials were heated, and at about 92° C., the reaction started. A total of 450 ml of propylene oxide were added as the mixture reacted, keeping the temperature at 106° C. The product, 669 g, was heated to 100° C. under full water aspirator vacuum. The product had a hydroxyl number of 250 and a total amine content of 2.1 meq/g.

EXAMPLE 2

Propoxylation of Tetraethylene Glycol Diamine Residue

To a one liter stirred autoclave were added 300 g of residues obtained by the reductive amination of tetraethylene glycol diamine. The analysis of these materials was: total acetylatables—7.08 meq/g; total amines—6.03 meq/g; and secondary and tertiary amines—3.14 meq/g. A total of 412 ml of propylene oxide was added at 110° C. The product was stripped at 100° C. and 35 mm pressure. The product weighed 551.7 g, and had a hydroxyl number of 306 and a total amine content of 3.13 meq/g.

EXAMPLE 3

Propoxylation of a Mixture of Residues

To a one liter stirred autoclave were added 156 g of triethylene glycol diamine residue and 152 g of tetraethylene glycol diamine residues. Propylene oxide (510 ml) was added over a six hour period at a temperature of 90°-94° C. After stripping, the product weighed 591.5 g. The product had a hydroxyl number of 280 and an amine content of 2.53 meq/g.

EXAMPLE 4

Propoxylation of Triethylene Glycol Diamine

Triethylene glycol diamine was propoxylated in a manner described above. The product had a hydroxyl number of 684 and an amine content of 6.68 meq/g.

EXAMPLE 5

Propoxylation of Tetraethylene Glycol Diamine

Tetraethylene glycol diamine was propoxylated in a manner described previously. The product was colorless, and had a hydroxyl number of 583, and 5.60 meq/g of amine.

EXAMPLE 6

Rigid Polyurethane Foams

The novel amino polyols of the present invention find particular utility as cross-linkers in the preparation of polyurethane foams. Tertiary amine groups are well known for their catalytic properties for the reaction of polyols and polyisocyanates to make polyurethanes. For more details on the various components and procedures in the production of polyurethane foams, examples of which will be presented herein, see U.S. Pat. Nos. 3,297,597 and 4,485,196, incorporated by reference herein, among others.

Rigid polyurethane foams were made using the amino polyols of Examples 1 through 5. Formulations were based on THANOL ®R-575 (sucrose/glycerin polyol) blended with known crosslinkers (THANOL ®SF-265 and VORANOL ®800) or the experimental crosslinkers prepared by the propoxylation of residues or pure compounds of the JEFFAMINE ®EDR series. The quantity of crosslinker used was the same in all cases on a hydroxyl basis.

Rigid polyurethane foams were prepared by standard one-shot, free-rise techniques using polymeric isocyanates. Formulation components were mixed at 2700 rpm and poured into an 8"×8"×12" (600 g pour) open mold and allowed to rise. Foams were cut into appropriate sizes and submitted for physical properties testing after standing at ambient conditions for a minimum of three days. The production of rigid polyurethane foams is well known in the art.

| Formulation, pbw | I | II | III | IV | V | VI | VII | VIII |
|---|---|---|---|---|---|---|---|---|
| Thanol R-575 (OH = 520) | 36.9 | 31.7 | 32.2 | 27.2 | 28.7 | 28.1 | 31.9 | 31.6 |
| Thanol SF-265 (OH = 635) | 5.0 | — | — | — | — | — | — | — |
| Voranol ® 800 (OH = 800) | — | 3.9 | — | — | — | — | — | — |
| Polyol Ex. 1 (OH = 250) | — | — | — | 14.3 | — | — | — | — |
| Polyol Ex. 2 (OH = 306) | — | — | — | — | 11.2 | — | — | — |
| Polyol Ex. 3 (OH = 279) | — | — | — | — | — | 12.5 | — | — |
| Polyol Ex. 4 (OH = 684) | — | — | — | — | — | — | 4.6 | — |
| Polyol Ex. 5 (OH = 583) | — | — | — | — | — | — | — | 5.4 |
| Silicone DC-193 ® | 0.5 | 0.5 | 0.5 | 0.5 | 0.5 | 0.5 | 0.5 | 0.5 |
| Freon R-11A | 13.0 | 13.0 | 13.0 | 13.0 | 13.0 | 13.0 | 13.0 | 13.0 |
| Thancat ® TD-33A | 1.5 | 0.7[1] | 0.7 | 0.7 | 0.7 | 0.7 | 0.7 | 0.7 |
| Rubimate ® M (I = 1.05) | 48.1 | 49.3 | 49.9 | 44.5 | 46.1 | 45.4 | 49.5 | 49.0 |
| Times | | | | | | | | |
| Mixing | 15 | 15 | 15 | 15 | 15 | 15 | 12 | 12 |
| Cream | 23 | 22 | 25 | 24 | 26 | 23 | 18 | 17 |
| Gel | 48 | 50 | 67 | 66 | 70 | 68 | 63 | 62 |
| Tack Free | 55 | 58 | 81 | 82 | 91 | 85 | 81 | 80 |
| Rise | 150 | 128 | 184 | 179 | 202 | 186 | 178 | 170 |
| Initial Surface | | | | | | | | |

-continued

| Formulation, pbw | Foam No. | | | | | | | |
|---|---|---|---|---|---|---|---|---|
| | I | II | III | IV | V | VI | VII | VIII |
| Friability | None | None | None | None | None | None | None | None |
| Foam Appearance | Good | Good | Good | Good | Good | Good | Good | Good |
| B-Comp. Appearance | OK | OK | OK | OK | OK | OK | OK | OK |
| Cell Structure | Good | Good | Good | Good | Good | Good | Good | |
| | | | | | | Good | | |
| Physical Properties | | | | | | | | |
| Density, pcf | 2.30 | 2.24 | 2.19 | 2.15 | 2.22 | 2.20 | 2.18 | 2.13 |
| K-Factor | 0.112 | 0.118 | 0.117 | 0.111 | 0.106 | 0.108 | 0.230 | 0.150 |
| Compressive Strength (psi) | | | | | | | | |
| With Rise | 39.57 | 39.53 | 36.67 | 35.97 | 38.99 | 39.05 | 32.52 | 33.80 |
| Against Rise | 14.11 | 14.79 | 14.10 | 13.26 | 13.19 | 12.34 | 17.11 | 14.10 |
| Heat Distortion, °C. | 188 | 194 | 194 | 160 | 168 | 158 | 193 | 186 |
| % Closed Cells | 90.76 | 90.55 | 89.95 | 93.43 | 93.62 | 94.66 | 64.55 | 86.31 |
| Friability | | | | | | | | |
| (% wt. loss, 10 min.) | 5.81 | 4.91 | 11.73 | 5.83 | 5.48 | 3.91 | 14.24 | 8.29 |

[1] Cup Foams were acceptable; planned 0.5 pbw catalyst; increased to 0.7; foams VII and VIII had isocyanate compatibility problems.

| | Dimensional Stabilities | | | | | |
|---|---|---|---|---|---|---|
| | ΔV | ΔW | ΔL | ΔV | ΔW | ΔL |
| | Foam I | | | Foam II | | |
| 158° F., 100% RH, 4 wks. | +7.1 | −3.0 | +4.0 | +4.2 | −2.1 | +2.9 |
| 200° F., dry, 1 week | +3.5 | −0.8 | +2.5 | +3.0 | −0.1 | +2.2 |
| −20° F., dry, 1 week | 0 | 0 | 0 | 0 | +0.1 | 0 |
| 158° F., 100% RH, 4 wks. | +10.0 | −4.2 | +5.8 | +6.6 | −3.0 | +4.4 |
| 200° F., dry, 4 weeks | +5.0 | −1.7 | +3.5 | +4.9 | −0.4 | +3.4 |
| | Foam III | | | Foam IV | | |
| 158° F., 100% RH, 4 wks. | +5.8 | −2.5 | +3.5 | +7.4 | −2.1 | +5.2 |
| 200° F., dry, 1 week | +3.4 | −0.4 | +2.5 | +4.7 | −0.3 | +3.4 |
| −20° F., dry, 1 week | 0 | +0.1 | 0 | 0 | +0.1 | 0 |
| 158° F., 100% RH, 4 wks. | +8.3 | −3.6 | +5.2 | +12.2 | −3.7 | +8.2 |
| 200° F., dry, 4 weeks | +5.2 | −1.2 | +3.8 | +9.8 | −0.9 | +6.5 |
| | Foam V | | | Foam VI | | |
| 158° F., 100% RH, 4 wks. | +8.0 | −2.7 | +5.0 | +8.8 | −3.6 | +5.5 |
| 200° F., dry, 1 week | +4.2 | −0.4 | +3.2 | +4.5 | −0.8 | +3.4 |
| −20° F., dry, 1 week | 0 | +0.1 | 0 | 0 | +0.1 | 0 |
| 158° F., 100% RH, 4 wks. | +12.1 | −4.3 | +7.5 | +12.6 | −5.6 | +8.0 |
| 200° F., dry, 4 weeks | +8.8 | −0.9 | +6.0 | +10.2 | −1.4 | +6.5 |
| | Foam VII | | | Foam VIII | | |
| 158° F., 100% RH, 4 wks. | +5.8 | −4.4 | +3.0 | +8.3 | −5.1 | +4.7 |
| 200° F., dry, 1 week | +1.3 | −2.3 | +0.8 | +4.2 | −1.1 | +2.7 |
| −20° F., dry, 1 week | 0 | −0.1 | 0 | 0 | +0.1 | 0 |
| 158° F., 100% RH, 4 wks. | +6.6 | −5.6 | +3.5 | +8.8 | −7.0 | +5.2 |
| 200° F., dry, 4 weeks | +1.5 | −3.5 | +1.2 | +6.1 | −2.4 | +4.0 |

Foams prepared from the residue-based crosslinkers prepared in accordance with the present invention, Foams IV, V and VI, gave better K-factors and closed cell contents, and otherwise comparable properties to those derived from the known crosslinkers, THANOL®SF-265 and VORANOL®800, used in Foams II and III, respectively.

| GLOSSARY | |
|---|---|
| THANOL® R-575 | Sucrose/glycerin polyol having hydroxyl number 520 made by Arco Chemical Co. |
| THANOL® SF-265 | Polyol having hydroxyl number 635 made by Arco Chemical Co. |
| VORANOL® 800 | Polyol having a hydroxyl number of 800, made by Dow Chemical; see structure presented earlier. |
| Silicone DC-193® | A silicone surfactant made by Dow-Corning Co. |
| Freon R-11A | Fluorocarbon 11 |
| THANCAT® TD-33A | A 33 wt. % solution of triethylenediamine in propylene glycol made by Texaco Chemical Co. |
| RUBIMATE® M | Polymeric MDI isocyanate, Rubicon Chemicals, Inc. |
| RH | Relative Humidity |

Many modifications may be made in the polyol mixtures of this invention and their method of production without departing from the spirit and scope of the invention, which is defined only in the appended claims. For example, one skilled in the art could adjust the temperature, pressure, reactants, proportions and modes of additions to provide polyol mixtures that give foams with optimal properties. It will further be appreciated that the method of the present invention makes beneficial use of the triethylene glycol diamine and tetraethylene glycol diamine bottoms products.

We claim:

1. Amino polyols prepared by the process comprising reacting an alkylene oxide with ethylene glycol diamine bottoms products, where the alkylene oxide is selected from the group consisting of ethylene oxide, propylene oxide, butylene oxide and mixtures thereof.

2. The amino polyols of claim 1 wherein the ethylene glycol diamine bottoms products are selected from the group consisting of triethylene glycol diamine bottoms products, tetraethylene glycol diamine bottoms products, and mixtures thereof.

3. The amino polyols of claim 1 wherein the reaction is conducted in the temperature range from about 80° to 150° C. at a pressure in the range from about atmospheric to 40 atmospheres.

4. The amino polyols of claim 1 wherein the mole ratio of the alkylene oxide to the ethylene glycol diamine bottoms products is approximately 3:1 to 6:1, based on active hydrogens bonded to nitrogen.

5. Amino polyols prepared by the process comprising reacting:
   an alkylene oxide, selected from the group consisting of ethylene oxide, propylene oxide, butylene oxide and mixtures thereof with
   ethylene glycol diamine bottoms products, selected from the group consisting of triethylene glycol diamine bottoms products, tetraethylene glycol diamine bottoms products and mixtures thereof
at a temperature in the range from about 80° to 150° C. and a pressure in the range from about atmospheric to 40 atmospheres.

6. The amino polyols of claim 5 wherein the mole ratio of the alkylene oxide to the ethylene glycol diamine bottoms products is approximately 4:1 to 5:1, based on active hydrogens bonded to nitrogen.

7. A method for producing amino polyols by reacting an alkylene oxide with ethylene glycol diamine bottoms products, where the alkylene oxide is selected from the group consisting of ethylene oxide, propylene oxide, butylene oxide and mixtures thereof.

8. The method of claim 7 wherein the ethylene glycol diamine bottoms products are selected from the group consisting of triethylene glycol diamine bottoms products, tetraethylene glycol diamine bottoms products, and mixtures thereof.

9. The method of claim 7 wherein the reaction is conducted in the temperature range from about 80° to 150° C. at a pressure in the range from about atmospheric to 40 atmospheres.

10. The method of claim 7 wherein the mole ratio of the alkylene oxide to the ethylene glycol diamine bottoms products is approximately 4:1 to 6:1, based on active hydrogens bonded to nitrogen.

11. A method for preparing amino polyols by reacting:
   an alkylene oxide, selected from the group consisting of ethylene oxide, propylene oxide, butylene oxide and mixtures thereof with
   ethylene glycol diamine bottoms products, selected from the group consisting of triethylene glycol diamine bottoms products, tetraethylene glycol diamine bottoms products and mixtures thereof
at a temperature in the range from about 80° to 150° C. and a pressure in the range from about atmospheric to 40 atmospheres.

12. The method of claim 11 wherein the mole ratio of the alkylene oxide to the ethylene glycol diamine bottoms products is approximately 4:1 to 6:1, based on active hydrogens bonded to nitrogen.

* * * * *